(12) United States Patent
Chi

(10) Patent No.: US 8,798,710 B2
(45) Date of Patent: Aug. 5, 2014

(54) APPARATUSES, SYSTEMS AND METHODS FOR BIOPOTENTIAL SENSING WITH DRY ELECTRODES

(71) Applicant: Yu Mike Chi, San Diego, CA (US)

(72) Inventor: Yu Mike Chi, San Diego, CA (US)

(73) Assignee: Cognionics, Inc., San Diego, CA (US)

( * ) Notice: Subject to any disclaimer, the term of this patent is extended or adjusted under 35 U.S.C. 154(b) by 0 days.

(21) Appl. No.: 13/656,598

(22) Filed: Oct. 19, 2012

(65) Prior Publication Data

US 2013/0102874 A1    Apr. 25, 2013

Related U.S. Application Data

(60) Provisional application No. 61/548,988, filed on Oct. 19, 2011.

(51) Int. Cl.
| | |
|---|---|
| *A61B 5/0408* | (2006.01) |
| *A61B 5/0478* | (2006.01) |
| *A61B 5/0492* | (2006.01) |
| *A61N 1/04* | (2006.01) |
| *A61B 5/04* | (2006.01) |
| *A61B 5/0488* | (2006.01) |
| *A61B 5/0476* | (2006.01) |
| *A61B 5/0402* | (2006.01) |

(52) U.S. Cl.
CPC ............ *A61N 1/0488* (2013.01); *A61B 5/0488* (2013.01); *A61N 1/0472* (2013.01); *A61B 2562/0209* (2013.01); *A61B 5/04* (2013.01); *A61B 5/0476* (2013.01); *A61B 5/0402* (2013.01)
USPC ........................... 600/396; 600/397; 607/149

(58) Field of Classification Search
CPC .. A61B 5/0408; A61B 5/0478; A61B 5/0492; A61B 2562/0209; A61B 2562/0214; A61B 2562/168
USPC .......... 600/372, 391, 392, 396, 397; 607/149, 607/152, 153
See application file for complete search history.

(56) References Cited

U.S. PATENT DOCUMENTS

| | | | | |
|---|---|---|---|---|
| 3,590,810 | A | * | 7/1971 | Kopecky ........................ 600/396 |
| 3,862,633 | A | * | 1/1975 | Allison et al. ................. 600/392 |
| 3,945,384 | A | * | 3/1976 | Topham ........................ 600/392 |
| 3,993,048 | A | * | 11/1976 | Francis ......................... 600/395 |
| 4,220,159 | A | * | 9/1980 | Francis et al. ................ 600/395 |
| 4,526,176 | A | * | 7/1985 | Bremer et al. ................ 600/392 |
| 4,669,479 | A | | 6/1987 | Dunseath, Jr. |
| 4,865,039 | A | | 9/1989 | Dunseath, Jr. |
| 5,421,982 | A | | 6/1995 | Ikeda et al. |
| 5,560,357 | A | * | 10/1996 | Faupel et al. ................. 600/345 |
| 6,418,333 | B1 | | 7/2002 | Axelgaard |

* cited by examiner

*Primary Examiner* — Lee S Cohen
(74) *Attorney, Agent, or Firm* — Edward W. Callan

(57) ABSTRACT

A biopotential electrode for transferring electrical signals with a subject that includes an electrical conductor, a membrane selectively permeable to ionic conduction for presenting a dry surface to the subject, and a conductive medium positioned in communication with a portion of the electrical conductor and a portion of the membrane. The electrical potentials are coupled from the subject across the membrane into the conductive medium and then transferred from the subject to the electrical conductor. In other embodiments, the electrical potentials may be transferred from the external conductor to the subject through the conductive medium across the membrane into the subject. Other embodiments include systems and methods for using the biopotential electrodes.

13 Claims, 1 Drawing Sheet

APPARATUSES, SYSTEMS AND METHODS FOR BIOPOTENTIAL SENSING WITH DRY ELECTRODES

CROSS-REFERENCES TO RELATED PATENT APPLICATIONS

The subject matter described in the present application is related to that described in the U.S. Patent Application No. 61/548,988 to Chi filed Oct. 19, 2011, now pending, which is incorporated by reference herein in its entirety.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND

Embodiments of the claimed subject matter relate to apparatuses and methods for improving the signal quality from dry biopotential sensors. Recording biopotential signals such as electrocardiograms (ECG), electroencephalograms (EEGs) or electromyograms (EMGs) conventionally require the use of a conductive "wet" electrode fixed to the body by an adhesive. The "wet" refers to the fact that a fluid—typically a liquid or gel—provides for a secure, low-resistance electrical connection between the body and the recording devices, ensuring a good signal. These conductive wet electrodes also typically require the use of an adhesive to keep the electrode stationary on the body.

However, the use of electrolytic gels and skin adhesives are messy, can be time consuming to apply, and often are prohibitively uncomfortable for long-term monitoring. Issues ranging from skin irritation from the electrode's gel to dry out and fall-off from daily use result in poor patient compliance and data loss.

In response to the limitations with wet adhesive electrodes, dry electrodes that do not require wet or gel media have recently been explored as alternatives. Before continuing, it is useful to clearly define the two types of biopotential electrodes commonly used. In the context of the present inventive subject matter and the field in general, skin-contact biopotential electrodes can be classified into types, consisting of 'wet' and 'dry'. As previously mentioned, wet type electrodes are commonly found in clinical and scientific applications and specifically require the application of a conductive fluid that is exposed onto the surface of the electrode and the subject's skin on use. The fluid may be an integral part of the electrode package (e.g., disposable ECG electrodes) or applied separately (e.g., standard reusable EEG cup electrodes). In all cases, the purpose of the conductive fluid is to lower the contact impedance between electrode and skin and facilitate signal transfer. A variety of fluids are possible ranging from saline (e.g., skin sweat) to specially formulated gels with high conductivity (e.g., EEG scalp cream). Other wet electrodes are not explicitly in liquid form and may utilize hydrogels, which nevertheless comprise largely of water and hydrate the surface of the skin. It is also possible to use simple tap water which itself is conductive due to it's impurities.

Dry electrodes, however, remove the need for the explicit application of a conductive fluid. In its simplest form, a dry electrode is a bare metal plate. The electrode operates immediately on contact with dry skin. It is important to note that dry electrodes still operate with an inherent amount of 'wetness.' In the case of the simple metal plate, ambient humidity from the atmosphere combined with moisture on the skin still help facilitate signal transfer. This is especially noticeable as sweat builds up over time, improving signal quality. The presence of 'moisture' is evident even in more sophisticated designs. As an example, micro-needle dry electrodes penetrate skin and leverage the water content under the skin for conduction.

The difference, however, between wet and dry electrode lies with the source of the fluid, it's application and its subjective feeling. In contrast to wet electrodes, dry electrodes do not require the specific application of a fluid or the exposure of 'wet' media onto skin. The dry electrode operates even if the skin and the surface of the electrode is dry (e.g., no sweat) and can be reused many times since there is no fluid to deplete. Finally the dry electrode simply feels 'dry' to the user since it does not introduce any additional moisture not commonly found on a resting subject. As a result, dry electrodes have many advantages in terms of comfort and longevity making them particularly well suited for long term monitoring applications. The main drawback is the apparent decrease in signal quality due to poor signal transfer, which the described embodiments of the inventive subject matter address.

Dry electrodes operate by sensing the same biopotential signals but through much higher electrode impedances, since conductive gel is not present. Compared to standard wet adhesive electrodes, dry electrodes are prone to a variety of signal quality issues including unstable offsets, high drifts, long-settling times and movement artifacts when used in the absence of adhesives. The majority of signal quality issues with dry electrodes arise from the poor quality of the dry skin-metal electrochemical interface. The standard wet Ag/AgCl electrode enables a consistently high signal quality due to the stability of the Ag/AgCl half-cell potential, which is buffered by a wet/gel electrolyte before contacting the skin. As a result, ionic charges in the body are readily converted to electronic signals through the low contact impedance of the wet gel. Dry electrodes, which typically include a bare metal 'disc', form an unstable interface with skin on contact due to the absence of an explicit buffering electrolyte. They must rely on ambient moisture and sweat in addition to parasitic capacitances to conduct potentials from the body. The lack of a buffering electrolyte manifests in drift noise, high contact impedances and susceptibility to movement artifacts. As a result, dry electrodes have not been well accepted for medical use due to the inferior signal quality compared to wet electrodes.

Prior art designs have tried to mitigate the signal quality issues by introducing a wetting agent, typically water, as a means to buffer a non-electrolytic interface. Kopecky (U.S. Pat. No. 3,590,810) describes a sensor comprising a cavity for storing electrolytes covered by a PTFE (Teflon™) membrane to seal the solution and present a conformable surface to the skin. However, the membrane required an externally applied wetting process (unless used on an already sweaty subject) in order to facilitate electrical conduction between the body and the electrode. Similarly, Brun del Re (U.S. Pub. No. 2004/0073104) discloses a design in which a superabsorbent polymer (SAP) is secured within a containment layer (preferred cotton fabric). The SAP is presoaked before usage and emanates moisture across the porous containment layer onto the skin to improve the coupling. However, these designs would still be classified as wet electrodes due to the intrinsic need for a fluid application on both the surface of the electrode and the skin. For long-term use, this poses comfort issues due to exposure of wet surfaces to the skin as well as usability issues arising from the need for fluid application (Kopecky) and replenishment (Brun del Re). Embodiments of the claimed subject matter include methods to implement a truly 'dry' electrode that can still achieve a similar contact quality as compared to standard wet electrodes without the use of a wetting agent/process or without introducing moisture onto the skin of the user. The embodiments are suitable for high quality, long-term monitoring applications.

SUMMARY

According to several aspects of the claimed subject matter, an apparatus is provided that includes three primary components. The first component is a connection to the electronic amplification circuitry, which may be implemented by means of a conductive base. The second component is a conductive gel or a wet medium that forms an electrochemical interface with the connection to the amplification circuitry. The third component is a membrane that permits exchange of ions between the body and the conductive medium while at the same time being sufficiently restrictive to block moisture such that the exterior face of the membrane presents a dry surface to the skin of the user. The electrode can be directly placed on dry skin without any wetting or preparation. Biopotential signals are coupled via the ionic conduction across the membrane from skin to the conductive media and converted to electronic signals Many of the embodiments include a biopotential electrode for transferring electrical signals with a subject that includes an electrical conductor, a membrane selectively permeable to ionic conduction for presenting a dry surface to the subject, and a conductive medium positioned in communication with a portion of the electrical conductor and a portion of the membrane. The electrical potentials are coupled from the subject across the membrane into the conductive medium and then transferred from the subject to the electrical conductor. In other embodiments, the electrical potentials may be transferred from the external conductor to the subject through the conductive medium across the membrane into the subject.

In some embodiments, the electrical potentials can be transferred from the external conductor to said subject through said conductive medium across said membrane into said subject and the electrical potentials can be coupled from said subject across said membrane into said conductive medium and then transferred from said subject to said electrical conductor. Also in some embodiments, the medium is hydrophilic for aiding in keeping the surface of the membrane dry. Embodiments may also include a membrane which is impermeable to the conductive medium for protecting the conductive medium and presenting a dry contact surface to the subject.

Embodiments may also include a membrane that is adhered to the conductive medium and several of the embodiments include a membrane that encapsulates the conductive medium for preserving and protecting the conductive medium. Many of the described embodiments use a conductive medium that is comprised of a gel or a fluid with ionic charge carriers. In one embodiment, the membrane is a dialysis tubing and in another embodiment, the biopotential electrode is connected to a high input impedance buffer amplifier. Another embodiment includes a electronic conductor that is comprised of a silver-silver chloride surface. Other embodiments include systems and methods for using the described biopotential electrodes.

DETAILED DESCRIPTION OF THE DRAWINGS

DETAILED DESCRIPTION OF THE EMBODIMENTS

Figure 1:
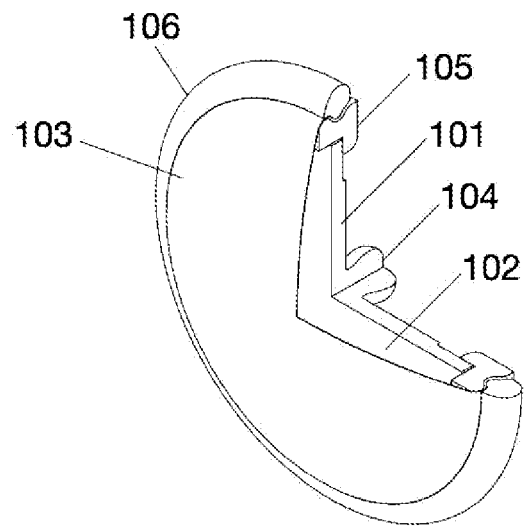
FIG. 1 is a side view of a sensor assembly showing the top plate, bottom plate, electrode, cable, opening, hollow interior, and elastic suspension system according to embodiments of the claimed subject matter.
Figure 2:
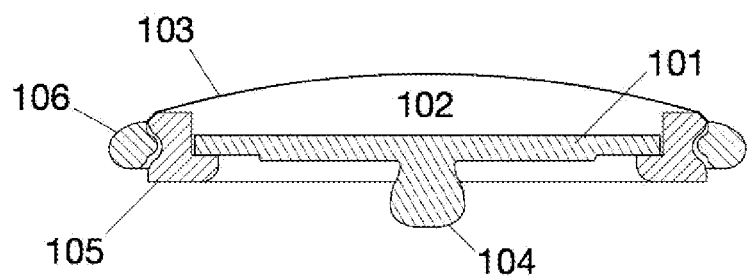
FIG. 2 is a side view of the sensor assembly of FIG. 1.
Figure 3:
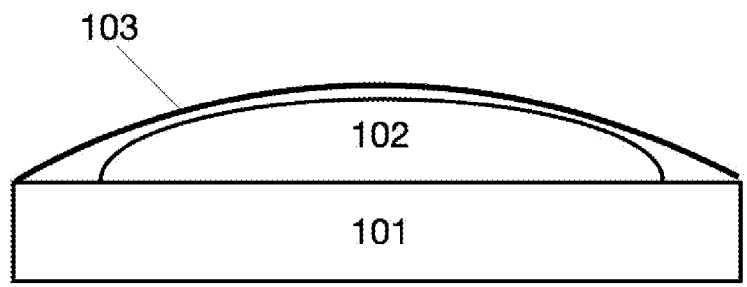
FIG. 3 is an illustration of another embodiment according to the claimed subject matter.

According to embodiments of the claimed subject matter, various apparatuses, systems and methods systems for constructing, mounting, and utilizing dry and/or non-contact electrodes are provided. The apparatuses and systems of the claimed subject matter may be generally described with the reference to FIGS. 1-3 showing, but not limited to, certain exemplary embodiments of the inventive subject matter.

In these embodiments, the dry electrode consists of an electrical conductor 101, for example an Ag/AgCl plate. The electrical conductor 101 is connected to subsequent amplification and other circuitry for signal acquisition. Other embodiments may utilize different electrical conductors instead of or in addition to an Ag/AgCl metal plate. For example, a plastic cup coated with Ag/AgCl, similar to standard ECG snap electrodes, can also be used. In another example, a gold cup or any other suitable conductor such as silver, tin, and other electrode materials known to those skilled in the art may be used instead of the Ag/AgCl metal plate. Other embodiments may include one or more fabric substrates which are printed Ag/AgCl or other metallic ink. In several of the embodiments, however, the use of Ag/AgCl results in a higher quality interface and hence lower noise and drift, producing a superior signal. The ultimate choice of electronic conductor 101 may depend on the desired cost, size and signal quality.

In the embodiments shown, the electrical conductor is depicted as a metal plate. Other structures are possible including one or more exposed wires, a micro needle array or a cup. The requirement is that the electrical conductor is in contact with the conductive medial 102. Selection of the shape will depend on the desired form-factor and size of the final product. Embodiments may be used in objects that come into contact with subjects. For examples, the embodiments may be added to or integrated within seats such as vehicle seats in cars, bikes and airplanes, chairs such as chairs in offices, clothing such as shorts and pants, headwear such as hats, watches, glasses such as goggles, prescription glasses, smart glasses, sunglasses and the like. Other examples of objects which may have embodiments attached or integrated within the objects include mattresses, linens, house goods such as pillows, tools, recliners and exercise related equipment such as embodiments integrated into treadmills or other fitness equipment. Similarly, embodiments may be integrated into covers for any object so that both signals can be communicated from the subject and to the subject. These embodiments may be further connected to systems for further analyzing and communicating the signals. Other embodiments may be used to send signals to the subject and other embodiments may be used to send and receive signals to the subjects. In one example, signals may be used to monitor a subjects health or a subject's sleep cycles and the return signals may also be used to alert the subject or to trigger an action by the user or by another user or device.

In the described embodiments, a conductive media 102 is deposited on the electronic conductor 101. In several of the embodiments, the conductive media 102 is an ECG electrode hydrogel (Skintact™ F-301) which can aid in conduction due to its high ionic content and compatibility with Ag/AgCl electrode interfaces. In addition, the hydrophilic properties of the solid ECG hydrogel ensures minimal moisture loss over time and these hydrophilic properties allow the embodiment's size and shape to be preserved over repeated usage. Other ECG-type hydrogels can also be utilized as they have the same or very similar electrical and mechanical properties. In addition, while other embodiments may use other conductive media such as saline or wet conductive gels (including those with different conductive properties), the solid hydrogel can be desirable for long-term monitoring applications since it retains water content better than other media.

In these embodiments, the conductive media 102 is enclosed by the ionic exchange membrane 103 to protect it from damage and to help retain its moisture content. The other side of the ionic exchange membrane 103 is the surface that contacts the skin and is dry by design and requires no wetting or application of a conductive fluid on usage. In the current embodiment, a dialysis membrane (SnakeSkin™ Dialysis Tubing, 10K MWCO) is used. The dialysis membrane has pores sufficiently large to allow exchange of ions making it nominally conductive.

At the same time, the dialysis membrane is sufficiently impermeable to both encapsulate the conductive media 102 and prevent leakage but to also help retain the moisture content of the conductive media 102. This extends the lifetime of the sensor and helps present a fully dry or at least drier surface positioned so that it is in communication with the skin of the subject. A drier surface would have a minimal amount of moisture, for instance the moisture from the subject's non-sweaty skin or the residual moisture from a wet swab in preparation for the application of the electrode.

In the embodiment just described, the electrode remains functional over a period of days, weeks or even months without the need for sealing or the need for moisture replenishment due to the highly hydrophilic properties of the hydrogel conductive media 102 and the relatively impermeable membrane (103). In the case of the embodiment currently described, samples over 6 months old stored in unsealed containers under standard office environments remained fully usable with no degradation of signal quality without any servicing or maintenance.

Although in these embodiments the ionic exchange membrane was implemented with dialysis tubing, other membranes (e.g., synthetics) could be utilized. Depending on the application, the membrane may be selected to optimize cost, flexibility, conductivity and/or biocompatibility.

As shown in FIGS. 1 and 2, a snap connector 104 is placed on the metal plate 103 for interfacing with standard ECG leads or any other type of interface thereby allowing many of the embodiments to be plugged in to standard ECG systems or any other type of signal processing device. Also shown is a plastic support 105 which is used to support the electronic conductor 101's structure. Also shown in this embodiment is an outer ring 106, which is affixed or snapped around the plastic support 105 for holding the ionic exchange membrane 103 in place.

FIG. 3 depicts another embodiment with fewer components but similar features. This embodiment shows an electrode containing an electronic conductor 101, a conductive media 102 and an ionic exchange membrane 103. Rather than using plastic supports to hold the membrane in place, the membrane is placed directly on top of the conductive medium 102, and held in place by the inherent tackiness of the conductive medium 102, simplifying its construction. For additional stability, the ionic exchange membrane 103 can also be attached to the edges of the electrode with an adhesive. As an example, one of the earliest embodiments was constructed by modifying a standard ECG electrode (Skintact™ F-301). An ionic exchange membrane, here dialysis tubing, was placed over the gel and surrounding adhesive foam to seal the gel inside the membrane. Another embodiment utilized a hydrogel electrode where the gel itself served as the adhesive and spanned the entire face of the electrode (3M 2670-5). This embodiment was implemented by laying the membrane over the gel without any other means for adhesion or sealing. In this embodiment, sealing the conductive medium 102 or trapping it within a cavity is not necessary if the medium 102 is a solid gel, which helps simplify construction. Another benefit of many embodiments is increased flexibility due to a fabric base which allows the embodiment to conform better to the subject's body.

As previously described, the embodiments of the inventive subject matter consist of an electrode formed by the layering of an electronic conductor 101, a conductive medium 102 and the ionic exchange membrane 103. The ionic exchange membrane 102 serves as a barrier for moisture and a protective covering for the conductive media 102. The result is that these embodiments present a dry electrode surface to the skin of the user, they maintain a greater comfort level for the user, and they aid in preserving the conductive media 102 for long-term monitoring applications. These embodiments are also electrically 'transparent' to ionic conduction while at the same time coupling biopotential signals from the body to the electronic conductor 101 for amplification and acquisition by electronic circuitry. They also offer a low-impedance, resistive contact with the skin, since the membrane is permeable to ionic charge carriers and offers a well defined electrochemical interface formed by the junction between the conductive media 102 and the electronic conductor 101.

Operation

In operation, the electrode is placed against the subject's skin with no wetting and with no preparation of either the electrode or the subject required. Biopotential signals from the body are exchanged across the membrane into the conductive media and to the electronic conductor. The electronic conductor is electrically connected to biopotential amplification circuitry that conditions and acquires the biopotential signal (e.g., ECG, EEG, EMG) for display, storage or analysis. After usage, the electrodes are simply removed from the user and can either be disposed of or cleaned, stored and reused. No servicing of the electrode, such as re-hydration, should be necessary over the lifetime of the device.

Since the electrode is non-adhesive, it is preferably used with a harness system that can secure the electrodes to the subject's skin comfortably. The system is ideally suited for long-term monitoring applications where standard wet electrodes pose comfort, convenience, and skin irritation issues. For further boosting the signal quality and rejecting artifacts, an active electronic amplifier with a high input impedance (>10 MOhm) may be placed nearby the electrode to buffer the signal and drive cables and wiring with a low-impedance output.

Although the embodiments are described used with dry skin-contact applications, many of the embodiments can also be used for dry non-skin contact sensing of bio-potential signals such as when used to sense signals through clothing or other materials. These embodiments also aid in the stabilization of the electrochemical interface even if the coupling is through high resistivity materials (e.g., cotton shirts.) They also allow for a more conformable surface than merely a bare metal plate to maximize coupling. Finally, the relatively low contact impedance of the electrode may also make it suitable for use in electro-stimulation applications where the use of a wet gel is not desirable.

Although the foregoing embodiments have been described in some detail by way of illustration and example for purposes of clarity and understanding, it will be apparent to those of ordinary skill in the art in light of the teaching of this inventive subject matter that certain changes and modifications may be made thereto without departing from the spirit or scope of the appended claims. For example, the embodiments may also be used with measurement of other systems and animals.

What is claimed is:

1. A biopotential electrode for transferring electrical signals with a subject comprising:
    an external electrical conductor;
    a membrane; and
    a conductive medium positioned in communication with a portion of said electrical conductor and a portion of said membrane;
    wherein electrical potentials can be coupled from said subject across said membrane into said conductive medium and then to said electrical conductor; and
    wherein the conductive medium is hydrophilic to ensure minimal moisture loss over time and the membrane permits exchange of ions between the subject's body and the conductive medium while at the same time being sufficiently restrictive to block moisture from the conductive medium such that the exterior face of the membrane presents a dry surface to the skin of the body.

2. The biopotential electrode of claim 1 wherein electrical potentials can be transferred from said external electrical conductor to said subject through said conductive medium and across said membrane into said subject.

3. The biopotential electrode of claim 1 wherein said membrane is impermeable to the conductive medium for protecting said conductive medium and presenting a dry contact surface to said subject.

4. The biopotential electrode of claim 1 wherein said membrane is adhered to said conductive medium.

5. The biopotential electrode of claim 1 wherein said membrane encapsulates said conductive medium for preserving and protecting said conductive medium.

6. The biopotential electrode of claim 1 wherein said conductive medium comprises a solid hydrogel with ionic charge carriers.

7. The biopotential electrode of claim 1 wherein said membrane comprises a dialysis tubing.

8. A monitoring system comprising:
    a biopotential electrode for transferring electrical signals with a subject; and a high input impedance buffer amplifier;
    wherein the biopotential electrode comprises: an external electrical conductor; a membrane; and a conductive medium positioned in communication with a portion of said electrical conductor and a portion of said membrane; wherein electrical potentials can be coupled from said subject across said membrane into said conductive medium and then to said electrical conductor; and wherein the conductive medium is hydrophilic to ensure minimal moisture loss over time and the membrane permits exchange of ions between the subject's body and the conductive medium while at the same time being sufficiently restrictive to block moisture from the conductive medium such that the exterior face of the membrane presents a dry surface to the skin of the body; and
    wherein said biopotential electrode is coupled to said high input impedance buffer amplifier.

9. The biopotential electrode of claim 1 wherein said electrical conductor includes a silver-silver chloride surface.

10. A method of detecting biopotential electrical signals from the skin of a subject, comprising the steps of:
    (a) positioning an electrode in communication with said subject's skin, said electrode comprising: an exterior electrical conductor; a membrane; and a conductive medium positioned in communication with a portion of the electrical conductor and a portion of the membrane; wherein electrical potentials can be coupled from said subject across said membrane into said conductive medium and then to said electrical conductor; and wherein the conductive medium is hydrophilic to ensure minimal moisture loss over time and the membrane permits exchange of ions between the subject's body and the conductive medium while at the same time being sufficiently restrictive to block moisture from the conductive medium such that the exterior face of the membrane presents a dry surface to the skin of the body;
    (b) receiving said electrical potentials coupled from said subject across said membrane into said conductive medium; and
    (c) transferring said electrical potentials from said subject to said electrical conductor.

11. The method of claim 10 wherein said membrane is impermeable to the conductive medium for protecting said conductive medium and presenting a dry contact surface to said subject.

12. The method of claim 10 wherein said membrane is adhered to said conductive medium.

13. The method of claim 10 wherein said membrane encapsulates said conductive medium for preserving and protecting said conductive medium.

* * * * *